US005733848A

United States Patent [19]
Luteri

[11] Patent Number: 5,733,848
[45] Date of Patent: Mar. 31, 1998

[54] PROCESS FOR MAKING MICROPARTICULATE AGRICULTURAL CHEMICALS

[75] Inventor: George F. Luteri, Mount Prospect, Ill.

[73] Assignee: Sandoz Ltd., Basel, Switzerland

[21] Appl. No.: 729,361

[22] Filed: Oct. 16, 1996

Related U.S. Application Data

[63] Continuation of Ser. No. 455,814, May 31, 1995, abandoned, which is a continuation of Ser. No. 261,314, Jun. 16, 1994, abandoned, which is a continuation of Ser. No. 936,687, Aug. 27, 1992, abandoned, which is a continuation-in-part of Ser. No. 714,406, Jun. 5, 1991, abandoned.

[51] Int. Cl.⁶ .......................... A01N 25/12; A01N 25/28; A01N 39/04
[52] U.S. Cl. ............................................ 504/116; 504/323
[58] Field of Search ..................................... 504/116, 323; 71/DIG. 1

[56] References Cited

U.S. PATENT DOCUMENTS

| | | | |
|---|---|---|---|
| 3,577,515 | 5/1971 | Vandegaer | 424/32 |
| 3,655,129 | 4/1972 | Seiner | 239/60 |
| 4,379,071 | 4/1983 | Schnorling et al. | 252/316 |
| 4,534,783 | 8/1985 | Beestman | 71/27 |
| 4,923,894 | 5/1990 | Kanda et al. | 514/493 |
| 4,936,901 | 6/1990 | Surgant, Sr. et al. | 71/92 |

OTHER PUBLICATIONS

Kirk–Othmer Encyclopedia of Chemical Technology, 3rd ed., vol. 18, "Polyesters Unsaturated", pp. 575–594.

*Primary Examiner*—S. Mark Clardy
*Attorney, Agent, or Firm*—Bell Seltzer Intellectual Property Law Group; Alston & Bird LLP

[57] ABSTRACT

Microparticulate agrochemicals based on crosslinked polyester polymers particularly suited to rapidly leaching herbicides.

9 Claims, No Drawings

PROCESS FOR MAKING MICROPARTICULATE AGRICULTURAL CHEMICALS

This is a CONTINUATION of Ser. No. 08/455,814, filed May 31, 1995, abandoned, which is a continuation of application Ser. No. 08/261,314 filed on Jun. 16, 1994, abandoned, which is a CONTINUATION of application Ser. No. 07/936,687, filed on Aug. 27, 1992, now abandoned which is a CONTINUATION-IN-PART of application Ser. No. 07/714,406 filed Jun. 5, 1991, now abandoned.

The present invention concerns microencapsulated agrochemicals, compositions containing them and processes for their production.

When putting agrochemicals in a suitable form for application, formulations are desirable which optimize the effect of the active ingredient on the target organism whilst at the same time minimizing its effect on the environment, particularly with respect to animals and plants which are not targeted. One such formulation technique which in recent years has been extensively investigated with respect to agrochemicals is microencapsulation. Various techniques for microencapsulation have been known for some time particularly in connection with pharmaceuticals and dyestuffs. Examples of such techniques are described eg in EP 148, 169; U.S. Pat. Nos. 4,417,916; 3,577,515; 4,354,783; 4,557, 755; 4,105,823: 3,516,941; EP 252,896; U.S. Pat. Nos. 4,601,863; 4,898,696.

A particular problem encountered with certain agrochemicals especially herbicides when applied to the soil is their tendency to leach rapidly from the target zone when subjected to rainfall or irrigation particularly in lighter soils which include coarse to moderately coarse texture soils and soils of low organic matter content, e.g. <2.0 weight % organic matter. This problem usually precludes or restricts the use of such agrochemicals for preemergent application. Thus in the case of a herbicide suffering from this drawback, persistence in the soil zone where germination of early weeds occurs can only be achieved, if at all, by repeated application or application at higher rates which increases the risk of damage to young crop plants or is uneconomical and environmentally undesirable.

In spite of the existence of many varied microencapsulation techniques, in some cases for decades, it has until now not been possible to provide a commercially viable microencapsulated form of such rapidly leaching agrochemicats which will achieve the four main objectives of maintaining weed control, reducing leaching below the targeted soil zone, increasing persistence in the soil, particularly the weed seed germination zone, and preventing crop injury.

It has now surprisingly been found that excellent results can be obtained by microencapsulating a rapidly leaching agrochemical in a crosslinked polyester polymer.

The present invention therefore provides a process for microencapsulating a rapidly leaching agrochemical comprising the steps of a) dissolving or suspending the agrochemical in a non-aqueous liquid mixture comprising unsaturated polyester resin and vinyl monomer;

b) emulsifying said solution or suspension in water to a desired particle size; and c) effecting crosslinking of the unsaturated polyester resin and vinyl monomer to produce the microcapsules.

Another aspect of the invention concerns an agricultural composition comprising a rapidly leaching agrochemical microencapsulated in an unsaturated crosslinked polyester/ vinyl polymer together with an agriculturally acceptable carrier.

A further aspect of the invention concerns a method of controlling undesirable pests or plant growth which comprises applying to the locus or anticipated locus of said undesirable pests or plant growth an effective amount of a rapidly leaching agrochemical microencapsulated in an unsaturated crosslinked polyester/vinyl polymer.

Microencapsulation according to the invention is particularly suited for agrochemicals where the usual locus of the pests or undesired plant growth to be combatted is in the upper layers of the soil. Microcapsules according to the invention can also be used in watery loci such as mosquito breeding areas or paddy fields.

Microencapsulation according To the invention is especially suited to agrochemicals where rapid leaching would normally preclude or restrict pro-emergent long lasting application. Examples of such agrochemicals are those containing a carboxylic acid group. Preferred examples of such compounds are herbicides particularly pro-emergent herbicides such as benzoic acid and phenoxycarboxylic acid derivatives e.g. dicamba, MCPA, 2,4-D. Examples of other herbicides which may benefit from encapsulation according to the invention include glyphosate, alachlor, acetochlor, metolachlor, chloropyridine carboxytates such as picloram, and 2-chloro-N-[1-methyl-2-methoxy]-N-(2,4-dimethyl-thien-3-yl)acetamide, which is described in U.S. Pat. No. 4,666,502.

The agrochemical may be in a solid crystalline or amorphous form or In liquid form, e.g. an oil. It is preferred that the agrochemical is soluble in the non-aqueous liquid comprising the unsaturated polyester resin and vinyl monomer and preferably only sparingly soluble in water. However, solid agrochemicals that are insoluble in the non-aqueous liquid comprising the unsaturated polyester resin and vinyl monomer may be encapsulated by grinding to an appropriate particle size and dispersing in the non-aqueous phase. Additionally liquid or solid agrochemicals with appreciable water solubility may also be encapsulated in the non-aqueous liquid comprising the unsaturated polyester resin and vinyl monomer if the aqueous phase is saturated with the agrochemical to prevent extraction from The non-aqueous phase. The agrochemical should be inert to free radical vinylic polymerization reactions and specifically should not contain vinylic groups.

Suitable forms of the aforementioned herbicides include the free acid, inorganic salts and amine salts. For the example of dicamba, the free acid, the iron, cobalt, nickel, manganese, zinc, triamylamine, dimethyldodecylamtne and dimethylhexadecylamine salts are soluble in the non-aqueous liquid comprising the unsaturated polyester resin and vinyl monomer and sparingly soluble in water. The aluminum salt of dicamba which is sparingly soluble in both water and the non-aqueous liquid comprising the unsaturated polyester resin and vinyl monomer, may be microencapsulated by dispersing the aluminum salt in the non-aqueous phase prior to dispersing the latter in the aqueous phase. Further water soluble salts such as lithium, sodium, potassium, magnesium and calcium salts of dicamba, may be microencapsulated by dispersing the salt in the non-aqueous liquid comprising the unsaturated polyester resin and vinyl monomer prior to dispersing the latter in an aqueous phase saturated with the same salt. The free acid and iron salt forms of dicamba, MCPA and 2,4-D are the preferred forms. Salts can be prepared in conventional manner.

Unsaturated polyester resins and crosslinked forms thereof with vinyl monomers as well as their preparation are known from the art, e.g. KIRKOTHMER Encyclopedia of Chemical Technology, 3rd ed. v. 18 pp. 575–594 which is incorporated herein by reference. They are macromolecules with polyester backbones derived from the interaction of unsaturated acids or anhydrides and polyhydric alcohols. They are mixed with vinyl monomers and may then be cured with free-radical initiators. The generation of free radicals from initiators maybe facilitated by promoters or accelerators, by radiation e.g. UV radiation or by heating. Detailed examples of each of these components are provided in the above mentioned reference.

The choice of acid, alcohol, vinyl monomer, initiator, etc., will be dictated as a rule by the nature of the product to be encapsulated and the desired properties and characteristics of the end-product. In the present invention an unsaturated polyester resin comprising fumaric and isophthalic acid with a glycol e.g. ethylene glycol is preferred. Such resins are often available in premixed commercial forms of unspecified detailed composition such as AROPOL™ resins (Ashland Chemicals), eg AROPOL™ 7242T-15, AROPOL™ 7241. The resins may already contain suitable promoters/accelerators preferably metal carboxylates e.g. cobalt carboxylates, or tertiary amines e.g. dimethyl aniline, but may also contain quaternary amine salts, strong acids or bases or clays.

Suitable vinyl monomers include styrene, divinylbenzene, vinyltoluene, alpha-methylstyrene, diallylphthalate and acrylates. The preferred vinyl monomer for use according to the invention is styrene. The vinyl monomer e.g. styrene is preferably present in the liquid resin at a concentration of from 25% to 60% by weight.

As discussed, curing of the resins is accomplished using an initiator that produces free radicals. It is preferred that such initiator be soluble in the non-aqueous liquid comprising the unsaturated polyester resin and vinyl monomer and be sparingly soluble in the aqueous phase. Examples of such preferred initiators include peroxyacids e.g. benzoyl peroxide, ketone peroxides e.g. methyl ethyl ketone peroxide, peroxyketals e.g. 1,1-di(tert-amylperoxy) cyclohexane (USP 90MD™, Witco), peroxyesters e.g. 2,5-dimethyl-2,5-di(2-ethylhexanoyl peroxy)hexane (USP245™, Witco) or tert-butyl peroxybenzoate (ESPEROX™-10, Witco), hydroperoxides e.g. cumene hydroperoxide, peroxycarbonates e.g. tert-butyl peroxy-2-ethylhexyl carbonate (ESPEROX™ C-496, Witco), dialkyl peroxides e.g. di-tert-butyl peroxide or azo compounds e.g. 2,2-azodiisobutyronitrile (FICEL™AZDN, Sherex). Water soluble free radical initiators such as hydrogen peroxide or persulphate salts may also be employed but are generally not preferred for suspension polymerizations. The various free radical initiators may be used singly or in combinations. One or more of the above mentioned promoters may be employed to aid in the generation of free radicals or the reaction may be simply heated to cause the initiators to generate free radicals, with or without the presence of promoters. Many of the above initiators are commercially available and are offered as formulations dissolved in or diluted by appropriate solvents such as dimethyl phthalate or mineral spirits.

In some cases curing may also be effected using UV light or other radiation such as X-rays.

Depending on the properties required of the microencapsulated product it may be desirable to dilute the unsaturated polyester resin/vinyl monomer with an appropriate nonvolatile solvent, oil or plasticizer. Examples of such diluents includes phthalate esters e.g. dimethylphthalate or dioctyl phthalate (Unocal Chemical Co.), glycol dibenzoates e.g. Benzoflex™ 9-88 (Velsicol Chemical Go.), alkyl aromatics e.g. T500-100 (Tenneco) or Aromatic 200 (Exxon Co.), or fatty acid esters e.g. methyl caprylate (Quantum) or methyl oleate (Emery).

In the emulsification phase of the process according to the invention the conditions are chosen such as to obtain the desired particle size which is preferably from 0.1 to 2000 micrometers, especially 2 to 100 micrometers, in particular 2 to 50 micrometers where spray application is envisaged. This is achieved by dispersing the oily phase in water using a suitable mixing or blending device such as a Waring blender or an Ika disperser or commercial scale blenders or mixers.

Advantageously the water may contain a surfactant or more preferably a dispersant. Examples of suitable dispersants are polyvinyl alcohols (e.g. Vinol®, Airvol®: Air Products), lignosulfonic acid salts (e.g. Reax®, Polyfon®: Westvaco), poly(methylvinylether/maleic acid) (Gantrez®, Agrimer VEMA®: GAF), polyethyleneoxtde/polypropyleneoxide block copolymers (e.g. Pluronic®: BASF), or naphthalene sulfonate-formaldehyde co-polymer (Daxad®: Grace).

The amount of active ingredient to be incorporated in the microcapsules will vary according to the final product desired, however, it has been found that amounts of up to 50% by weight of a.i. may be successfully microencapsulated with ease. The active ingredient content of the microcapsules maybe determined by extraction with a suitable solvent and analyzing the resultant solution by HPLC using either an internal or external standard.

The microcapsules may be isolated from the reaction by conventional techniques e.g. by filtration, by centrifugation and/or by drying (e.g. spray drying) or may be left suspended in the aqueous phase.

To facilitate application the microcapsules of the invention may be formulated in conventional manner, by simple spray-drying or, depending on intended application, solid or liquid form such as dusts, granules, solutions, emulsions, wettable powders or flowables, suspensions and the like with conventional carriers and optionally other adjuvants. Such formulated microcapsules may be prepared in conventional manner e.g. by mixing, spray-drying and the like.

Application of the microcapsules of the present invention is made according to conventional procedure to the weeds or pests or their locus using an effective equivalent amount of active ingredient.

In the case of commercial available products, the effective amount will be based on the a.i. content and release profile of the microcapsule to correspond to the known effective application rate e.g. in the case of dicamba 0.05 to 2 lb/ac (approximately 0.055 to 2.2. kg/ha), especially 0.1 to 1 lb/ac (approximately 0.11 to 1.1 kg/ha). The optimum usage of the microcapsules of the present invention is readily determined by one of ordinary skill in the art using routine testing such as column leach testing, greenhouse testing and small plot testing.

For example, in the pre-emergent control of weeds a half-life of from 7–60 days, preferably 40–60 days would be desirable (time required for 50% of a.i. to be released from the microcapsule).

Suitable formulations contain from 0.01 to 99% by weight of active ingredient equivalent from 0 to 20% of surfactant and from 1 to 99.99% of solid or liquid diluent(s). Higher ratios of surfactant to active ingredient are sometimes desirable and are achieved by incorporation into the formulation or by tank mixing. Application forms of a composition generally contain between 0.01 and 80% e.g. 0.01 to 25% by weight equivalent of active ingredient. Lower or higher levels of active ingredient can, of course, be present depending on the intended use, the physical properties of the microcapsules and the mode of application. Concentrate forms of a composition intended to be diluted before use generally contain between 2 and 90% preferably between 5 and 81% by weight equivalent of active ingredient.

The microcapsules covered in this invention may also be used to encapsulate cyclodextrin or other macrocyclic complexes of agrochemicals.

Agriculturally acceptable additives may be employed in the composition to improve performance and to reduce foaming, caking, settling and corrosion, for example.

"Surfactant" as used herein means an agriculturally acceptable material which imparts emulsifiability, spreading, wetting, dispersibility or other surface-modifying properties. Examples of such surfactants are naphthalene sulfonates, sulfosuccinates, alkylsulfonates, fatty ester sulfates, ethoxylated alcohol sulfates and sulfonates, fatty alcohols, ethoxylated alcohols, glycerides and fatty acids and phosphated esters, ethers, alcohols or acids.

"Diluent" as used herein means a liquid or solid agriculturally acceptable material used to dilute a concentrated material to a usable or desirable strength. For dusts or granules it can be e.g. talc, clays, diatomaceous earth, cellulose, starch or fine organic matter such as ground corn cobs or grain hulls. For liquid concentrate forms it can be eg vegetable oils, mineral oils (either aliphatic or aromatic) alcohols, ketones, ethers, esters or heterocyclic compounds, and for liquid application forms eg water or mineral or vegetable oils.

Microcapsule formulations may optionally contain further active ingredient such as other herbicides, insecticides, acaricides, fungicides and the like. For example, it may be advantageous to formulate microcapsules according to the invention together with the same or other active ingredient in unencapsulated form to achieve initial control prior to the onset of controlled release from the microcapsules or to provide a wider or different spectrum of control than that provided by the microencapsulated material. Such unencapsulated material may be dry blended with the microcapsules, may be incorporated into water dispersable or nondispersable granules along with the microcapsules or may be applied as a coating on the microcapsules eg via spray drying. Alternatively, premix or tank-mix of unencapsulated with encapsulated material can be appropriate.

Combinations of unencapsulated and encapsulated material should be formulated in amounts and applied at rates sufficient to achieve initial weed control without causing undue crop damage. In the case of dicamba, satisfactory results are achieved when the unencapsulated form is applied at a rate ranging from about 0.125 to 0.25 lb/ac (about 0.138 to 0.28 kg/ha) whilst the encapsulated form is applied at a rate of up ro about 1.0 lb a.i./ac (about 1.1 kg a.i./ha). Thus, suitable weight ratios for formulations containing unencapsulated and encapsulated material eg dicamba range from 1:8 to 1:1 eg 1:8 to 1:4 or 1:4 to 1:1 unencapsulated: encapsulated a.i.

As a further alternative a formulation may consist of a mixture of microcapsules having various pre-polymer to a.i. weight ratios.

Combinations mentioned above can allow for effective, continuous control over periods as long as 1 to 75 days.

The following examples illustrate the invention. Temperatures are given in degrees centigrade.

EXAMPLE 1

Preparation of dicamba microcapsules a) Preparation of aqueous phase:

Dissolve 2.7 g Airvol™-523 polyvinyl alcohol (Air Products) in 266 g distilled water by adding the Airvol™-523 to the stirred water at ambient temperature and warming with stirring to 80° C. for about 1 hour to complete the dissolution. Cool the solution to ambient temperature and add 1.3 g Gantrez™ S-95 methyl vinyl ether/maleic acid copolymer (GAF) with stirring to the polyvinyl alcohol solution. Warm with stirring to 80° C. for about 0.5 hour to complete the dissolution. Cool to ambient temperature for storage.

b) Preparation of the non-aqueous phase:

Dissolve 75.0 g of 90% assay technical dicamba acid in 195 g of Aropol™ 7242T-15 polyester/styrene liquid resin (Ashland Chemicals). Stirring and warming to 40°–50° C. conveniently effects the dissolution. Cool to ambient temperature for storage.

c) Preparation of microcapsules:

Charge a 1000 ml stainless steel or glass Waring blender cup with 270 g of the above aqueous phase. In a separate container thoroughly mix 4.0 g of USP-245® peroxyester (Whitco) with 270 g of the above non-aqueous phase. Begin blending the aqueous phase at about 20% of maximum speed and add the non-aqueous phase to the aqueous phase. Increase the blending speed to about 50% of maximum and blend for about 8 minutes. Stop the blender and transfer the resulting emulsified mixture to a glass or stainless steel reaction flask. Add 5.4 g of Reax™ 88B lignosulfonate (Westvaco). Stir the mixture and warm to 70° C. for 4 hours. Cool to ambient temperature.

d) Measurement of particle size:

The average particle size and particle size distribution of the above preparation may be measured by standard techniques such as: optical or electron microscopy, light scattering or conductometric measurements.

e) Control of particle size:

The average particle size and particle size distribution may be conveniently controlled by known techniques such as by the rate of shear provided by the blender or mixer and by the concentration and type of dispersants employed. See R. Arshady and A. Ledwith, *Reactive Polymers*, 1, p. 159–174 (1983), Lj. M. Djakovic, P. D. Dokic and I. B. Sefer, *J. Dispersion Science and Technology* 10(1), p. 59–76 (1989) and J. M. Church, *Chemical Engineering*. p. 79 August 1 (1966).

f) Measurement of completeness of crosslinking:

Unreacted styrene monomer may be conveniently measured by azeotropically distilling the styrene from a sample of the reaction suspension. For the above example, a 250 ml 3-neck flask is charged with a 50 g sample of the reaction mixture along with 50 g of distilled water. The mixture is warmed with stirring to 100° C. The styrene/water azeotrope is collected at 93.9° C. through a short path distillation head. The distillation is continued until water is collected at 100° C. The styrene may be conveniently measured using a graduated collection flask.

g) Concentration of active ingredient in microcapsules:

In the above example the concentration of dicamba in the microcapsules was 25% by weight of the AROPOL™7242T-15. This concentration may be increased or decreased as desired. The concentration may be increased by simply dispersing finely divided solid dicamba in liquid polyester/styrene resin at the desired concentration such that some is dissolved and some is dispersed as solid particles. It is preferred however that all of the dicamba be dissolved in the liquid polyester/styrene resin prior to formation and cross-linking of the micro-capsules. This may conveniently be accomplished by warming the mixture of dicamba and liquid polyester styrene resin so as to increase the solubility of dicamba. This is illustrated in Example 2.

EXAMPLE 2

Preparation of dicamba microcapsules a) preparation of aqueous phase:

Dissolve 2.50g of Airvol™-523 polyvinyl alcohol (Air Products) and 1.25g of Gantrez™S-95 methyl vinyl ether/maleic acid copolymer (GAF) and 1.00g Reax™915 lignosulfonate (Westvaco) in 195.25g of distilled water by adding the solids to the water at ambient temperature with stirring. Complete dissolution by warming to 80° C. with stirring for about 0.5 to 1.0 hours. Hold at 80° C.

b) Preparation of the non-aqueous phase:

Charge a 500 ml cylindrical flask with 100.0g of 90% assay dicamba acid and 100.0g Aropol™7241 polyester/styrene liquid resin (Ashland Chemicals). Warm with stirring to 80° C. to dissolve the dicamba acid. Hold at 80° C.

c) preparation of the microcapsules:

While stirring the non-aqueous phase at 80° C. add 4.0 g of Esperox™10 tert-butyl peroxybenzoate (Witco). Stir for 3.0 minutes to ensure even dissolution. Stop the stirrer, add the above 200.0 g of aqueous phase and disperse the non-aqueous phase in the aqueous phase using the Ika S25N-25F Ultra-Turrax™disperser operating at about 45% of maximum speed for 2.0 minutes. Remove the dispersing tool and continue stirring the reaction at 80° C. for 1.0 hour. Cool to ambient temperature. Control and measurement of particle size and determination of completeness of polymerization may be achieved as described above.

EXAMPLE 3

Assay for active ingredient content

The active ingredient content of the microcapsules is determined by extraction with a suitable solvent and analyzing the resultant solution by HPLC using either an internal or external standard. For example in the case of dicamba acid encapsulated in AROPOL™ 7242T-15 0.1 to 0.4 g of capsules are suspended in 100.0 ml of methanol and shaken for 1 to 24 hours. The extracted capsules are allowed to settle and 20.0 ml of clear supernatant drawn by piper. An appropriate internal standard such as a halophenol or halobenzoic acid preferably para-bromophenol is added and the extract analyzed by HPLC. Suitable instrument operating parameters include a 4.6 mm×150 mm $C_{18}$ reverse phase column, eluting with a mobile phase initially comprising 60% of 2% aqueous acetic acid and 40% methanol programmed to 90% methanol over 20 minutes, at a flow rate of 1.0 ml per minute. Using an ultra violet detector at 280 nanometers dicamba is detected at 9.6 minutes and para-bromophenol at 12.5 minutes. Alternatively for example in the case of dicamba acid encapsulated in AROPOL™7241 suspend 0.1 to 0.4 g of capsules in about 90ml of tetrahydrofuran and add an appropriate amount of 3,5-dichlorobenzoic acid as an internal standard. Shake at ambient temperature for 0.5 to 1.0 hour. Withdraw about 5 ml of sample and dilute with about 5ml of 1:1 methanol/water. Filter and analyze by HPLC. Suitable instrument conditions include a 4.6 mm×150 mm $C_{18}$ reverse phase column, eluting with a mobile phase initially comprising 60% of 2% aqueous acetic acid and 40% methanol programmed to 90% methanol over 20 minutes at a flow rate of 1.0 ml per minute. Using an ultraviolet detector at 280 nanometers dicamba is detected at 5.6 minutes and 3,5-dichlorobenzoic acid at 12.5 minutes.

EXAMPLE 4

Method for measuring the rate of release from the microcapsules

A convenient method for characterizing the rate at which the active ingredient releases from the microcapsules is illustrated by the following example for dicamba: A quantity of microcapsules containing 0.005 g of dicamba is weighed into a 2 oz bottle and 50.0 g distilled water added. The sample is placed in a constant temperature bath at 30° C. and shaken at 100 oscillations per minute. At various times 3 ml aliquots are drawn from the sample and filtered through a 0.2 micrometer cellulose acetate membrane filter to remove the microcapsules. The filtered samples may then be analyzed by HPLC against an external or internal standard.

EXAMPLE 5

Formulation as wettable powder

The following components are combined to yield a wettable powder.

a) Microcapsules according to Example: 94% b) Aerosol® OT-B (Sodium dioctyl sulfosuccinate: American Cyanamid): 3% and c) Morwet® D425: (Sodium naphthalene formaldehyde condensate: Whitco): 3%

The inerts are preground before mixing with microcapsules to avoid capsule breakage.

EXAMPLE 6

To 100 parts of the microcapsule slurry in Example 1 add 0.075 parts Kelzan®S xanthan gum (Kelco division of Merck & Co.) and mix for 0.25 to 1.0 hour to disperse and dissolve the Kelzan®S. This will yield a microcapsule suspension concentrate that resists settling by the particles and may be diluted easily with water to yield a sprayable suspension.

EXAMPLE 7

Evaluation of leaching characteristics

Glass leaching columns, 5-cm long and 9-cm diameter, are packed with soil to achieve a bulk density of approximately 1.4 g/cm$^3$, which is similar to that in a field. The soil consists of 72.1% sand, and 16.9% silt and 11.0% clay. The organic matter content is 1.8% and the pH is 7.5%.

The columns packed with soil are first saturated with water by allowing about 400 mls of deionized water to leach through them. Excess water is allowed to drain out of the columns by leaving them undisturbed overnight. The soil surface in each column is then sprayed with 5-ml solutions of the formulations containing 2.5 mg a.e. (corresponding to 4 kg a.e./ha) using an atomizer (3 columns for each formulation and 3 control columns). Treated columns are then leached with 85, 170, or 510 mls of water corresponding to 0.5, 1.0, or 3.0 inches rainfall equivalent. The flow rate of water is adjusted to approximately 1 ml/min. The leachate from each column is collected and analyzed using high performance liquid chromatography (HPLC) with the leachates from uncreated control columns being used for calibration. After the first irrigation the columns are wrapped in aluminum foil to prevent excessive loss of moisture and to exclude light and incubated in a growth room set at 24° C. for 2 weeks and again irrigated. The procedure is repeated for a third time following an additional 2 week incubation.

Results

| irrigation amount | form | Amount of dicamba released (mg) | | | % release of total applied |
|---|---|---|---|---|---|
| | | 1st irrigation | 2nd irrigation | 3rd irrigation | |
| 0.5 inch | A | 0.7 | 1.3 | 0.6 | 104% |
| | B | 0.2 | 0.9 | 0.9 | 80% |
| 1.0 inch | A | 2.7 | 0.0 | 0.0 | 108% |
| | B | 0.4 | 1.1 | 0.1 | 64% |
| 3.0 inch | A | 2.6 | 0.1 | 0.0 | 108% |
| | B | 0.6 | 0.7 | 0.1 | 56% |

A = Banvel ® (dicamba (as DMA salt) in regular commercial form)
B = Formulation prepared according to the method of Example 1.

What is claimed is:

1. A process for making microparticles incorporating a rapidly leaching agrochemical comprising the steps of
   a. dissolving or suspending the agrochemical in a non-aqueous liquid mixture comprising unsaturated polyester resin and vinyl monomer;
   b. emulsifying said solution or suspension in water to and about 50 micrometers; and
   c. effecting crosslinking of the unsaturated polyester resin and vinyl monomer to produce the microparticles.

2. A process according to claim 1 wherein the agrochemical is soluble in the non-aqueous liquid mixture and only sparingly soluble in water.

3. A process according to claim 2 wherein the agrochemical is selected from dicamba; MCPA and 2,4-D.

4. A process according to claim 1 wherein the vinyl monomer is styrene.

5. A process according to claim 1 wherein the unsaturated polyester resin comprises fumaric and isophthalic acid with a glycol.

6. A process according to claim 1 wherein curing of the resin is accomplished using an initiator.

7. A process according to claim 6 wherein curing is accomplished by using an initiator selected from the group consisting of peroxyacids, ketone peroxides, peroxyketals, peroxyesters, hydroperoxides, peroxycarbonates, dialkylperoxides or azo compounds.

8. A process according to claim 1 carried out in the presence of a promoter selected from a metal carboxylate, a tertiary amine, a quaternary amine salt, a strong acid or base or a clay.

9. A process according to claim 1 wherein the promoter is a cobalt carboxylate.

* * * * *